US008701963B2

(12) United States Patent
Bach et al.

(10) Patent No.: US 8,701,963 B2
(45) Date of Patent: Apr. 22, 2014

(54) MEDICAL ANASTOMOSIS APPARATUS (75) Inventors: Du-Jin Bach, Seoul (KR); Sung Min Kim, Gyeonggi-do (KR); Jae-Sung Choi, Seoul (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/515,785

(22) PCT Filed: Feb. 23, 2011

(86) PCT No.: PCT/KR2011/001173
§ 371 (c)(1),
(2), (4) Date: Jun. 12, 2013

(87) PCT Pub. No.: WO2012/067310
PCT Pub. Date: May 24, 2012

(65) Prior Publication Data
US 2013/0264371 A1 Oct. 10, 2013

(30) Foreign Application Priority Data
Nov. 15, 2010 (KR) .................. 10-2010-0113409

(51) Int. Cl.
*A61B 17/115* (2006.01)
(52) U.S. Cl.
USPC .............. 227/179.1; 227/176.1; 606/153
(58) Field of Classification Search
USPC ................ 227/176.1, 179.1; 606/153
See application file for complete search history.

(56) References Cited

U.S. PATENT DOCUMENTS

| 5,188,638 | A | * | 2/1993 | Tzakis ........................ 606/153 |
| 5,314,436 | A | * | 5/1994 | Wilk ............................ 606/153 |
| 5,346,115 | A | * | 9/1994 | Perouse et al. ............. 227/179.1 |
| 5,395,030 | A | * | 3/1995 | Kuramoto et al. ......... 227/179.1 |
| 5,720,755 | A | * | 2/1998 | Dakov ......................... 606/139 |
| 7,585,307 | B2 | * | 9/2009 | Fontayne et al. ............. 606/153 |
| 2006/0000869 | A1 | * | 1/2006 | Fontayne ................... 227/175.1 |
| 2010/0114121 | A1 | | 5/2010 | Hochstadter et al. |
| 2010/0224668 | A1 | * | 9/2010 | Fontayne et al. .......... 227/175.2 |

FOREIGN PATENT DOCUMENTS

| EP | 1621139 A2 | 2/2006 |
| JP | 2009-066424 | 4/2009 |
| JP | 2009-066424 A | 4/2009 |

(Continued)

OTHER PUBLICATIONS

International Search Report mailed Dec. 22, 2011 for International Application No. PCT/KR2011/001173.

*Primary Examiner* — Andrew M Tecco
(74) *Attorney, Agent, or Firm* — Swanson & Bratschun L.L.C.

(57) ABSTRACT

A medical anastomosis apparatus is provided. The medical anastomosis apparatus includes a cylindrical body which has a hollow portion and extends in a longitudinal direction, a pressing rod which is provided inside of the hollow portion of the body to translate along the hollow portion, a knob which is coupled to the pressing rod to provide a driving force to translate the pressing rod, a guide member which is inserted into one end of the body and simultaneously coupled to expose a portion of the body and has a pressing unit formed therein to move radially upon translation of the pressing rod, and a staple cartridge which is inserted around an outer circumferential surface of the guide member and then coupled to the body and has built-in staple clips that protrude outward upon movement of the pressing unit.

9 Claims, 5 Drawing Sheets

(56) References Cited

FOREIGN PATENT DOCUMENTS

| | | |
|---|---|---|
| KR | 10-2006-0048860 | 5/2006 |
| KR | 10-2007-0108134 | 11/2007 |
| WO | WO 2006-027014 A1 | 3/2006 |

* cited by examiner

MEDICAL ANASTOMOSIS APPARATUS

CROSS-REFERENCE TO RELATED APPLICATION

This application is a 35 U.S.C. §371 national phase application of PCT/KR2011/001173 (WO 2012/067310), filed on Feb. 23, 2011, entitled "Medical Anastomosis Apparatus", which application claims priority to and the benefit of Korean Patent Application No. 2010-0113409, filed Nov. 15, 2010, the disclosure of which is incorporated herein by reference in its entirety.

BACKGROUND

1. Field of the Invention

The present invention relates to a medical anastomosis apparatus, and more particularly, to a medical anastomosis apparatus capable of radially sewing an overlapping part in a state in which a blood vessel overlaps another blood vessel, a blood vessel overlaps an artificial blood vessel, an organ overlaps another organ or an organ overlaps a blood vessel.

2. Discussion of Related Art

Arterial obstructive diseases, which develop by narrowing and occlusion of blood vessels, increase every year due to lack of exercise and westernized diets.

In particular, representative examples of heart diseases generally include myocardial infarction and angina pectoris, both of which are caused by ischemia in which blood vessels through which nutrition and oxygen are supplied to the heart are occluded.

A surgical operation is often used to treat an occlusive blood vessel or a substantially occluded blood vessel. Such a surgical operation includes end-to-end anastomosis which includes incising an affected part of a blood vessel and anastomosing the incised blood vessel. In this case, when a long portion of the blood vessel is incised, or a long blood vessel is required to bypass the affected part of the blood vessel, a vein in the leg is generally incised and used.

A section of blood vessels is mainly composed of intima, media and adventitia. When two blood vessels are anastomosed, it is necessary to anastomose the blood vessels in a state in which one intima is closely attached to the other intima.

However, upon the anastomotic operation of the incised blood vessel as well as the treatment of such arterial obstructive diseases of the heart, a medical specialist in microsurgeries directly secures the vision for surgery under a microscope or a high-powered magnifying glass, and then manually stitches the incised blood vessels using a stitching fiber. Therefore, this stitch surgery has problems in that it should be performed by a highly skilled medical specialist, and also requires a great deal of time and effort.

In particular, it is very difficult to stitch anastomose blood vessels one by one in organs (for example, the heart) which pulse continuously and regularly. Therefore, it is necessary to artificially induce paralysis of the heart and stop the heartbeat for at least 3 hours during heart surgery.

Therefore, a variety of anastomosis apparatuses have been designed to avoid manually stitching blood vessels one by one using such stitching fiber. Among these, apparatuses capable of easily anastomosing blood vessels in an end-to-end manner are disclosed in U.S. Pat. Nos. 3,774,615, 4,214,586 and 4,917,087, and a microvascular anastomotic coupler is, for example, commercially available from Synovis Micro Companies Alliance (US).

U.S. Pat. No. 3,774,615 discloses an apparatus for anastomosing cut blood vessels without surgery. However, the apparatus has problems in that the blood vessels are not completely anchored in a site in which the blood vessels are anastomosed, it is difficult to evenly attach the peripheries of two cut blood vessels, and a contact region between the cut blood vessels is very small in area, which leads to poor anastomosis and blood leakage.

U.S. Pat. No. 4,214,586 proposes an apparatus which is similar to that of U.S. Pat. No. 3,774,615 in basic principle. Here, the apparatus is configured to securely anchor end portions of the cut blood vessels. However, the apparatus has a problem in that, since a contact region between the cut blood vessels is small in area, it is difficult to anastomose the blood vessels.

Meanwhile, the above-described stitching technique includes a method of stitching blood vessels using a stapling device that uses a surgical staple. Such a method has been used for gastrointestinal resection and anastomosis, lung resection, bronchorrhaphy and skin closure.

However, the stapling device is generally a linear staple that is widely used for longitudinal resection and stitching.

Accordingly, the conventional stapling device may not easily apply to anastomosis between circular blood vessels and blood vessels, or blood vessels and artificial blood vessels.

Furthermore, the conventional stapling device has difficulties in anastomosing blood vessels with an organ, for example, the gastrointestinal tract, the lungs or the bronchus, or anastomosing an organ with another organ.

SUMMARY OF THE INVENTION

The present invention is directed to providing a medical anastomosis apparatus which is able to rapidly and safely perform a complicated reinforcing/anastomosis procedure that includes reinforcing an aortic resection site and anastomosing an artificial blood vessel upon gastrointestinal resection and anastomosis, lung resection, bronchorrhaphy, skin closure, acute aortic dissection, or surgery of thoracic and abdominal aortic aneurysm.

One aspect of the present invention provides a medical anastomosis apparatus including:

a cylindrical body which has a hollow portion and extends in a longitudinal direction;

a pressing rod which is provided inside the hollow portion of the body to translate along the hollow portion;

a knob which is coupled to the pressing rod to provide a driving force to translate the pressing rod;

a guide member which is inserted into one end of the body and simultaneously coupled to expose a portion of the body and has a pressing unit formed therein to move radially upon translation of the pressing rod; and a staple cartridge which is inserted around an outer circumferential surface of the guide member and then coupled to the body and has built-in staple clips that protrude outward upon movement of the pressing unit.

BRIEF DESCRIPTION OF THE DRAWINGS

The above and other objects, features and advantages of the present invention will become more apparent to those of ordinary skill in the art by describing in detail the exemplary embodiments thereof with reference to the attached drawings, in which.

DETAILED DESCRIPTION OF EXEMPLARY EMBODIMENTS

Hereinafter, the exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and similarly, a second element could be termed a first element, without departing from the scope of the exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid understanding of the present invention, like numbers refer to like elements throughout the description of the figures, and the description of the same elements will be not reiterated.

The present invention is directed to providing a medical anastomosis apparatus. Here, the medical anastomosis apparatus includes a cylindrical body which has a hollow portion and extends in a longitudinal direction, a pressing rod which is provided inside the hollow portion of the body to translate along the hollow portion, a knob which is coupled to the pressing rod to provide a driving force to translate the pressing rod, a guide member which is inserted into one end of the body and simultaneously coupled to expose a portion of the body and has a pressing unit formed therein to move radially upon translation of the pressing rod, and a staple cartridge which is inserted around an outer circumferential surface of the guide member and then coupled to the body and has built-in staple clips that protrude outward upon movement of the pressing unit.

The medical anastomosis apparatus according to the present invention is used for surgery to anastomose a blood vessel with another blood vessel or a blood vessel with an artificial blood vessel, preferably reinforcing an aortic resection site and anastomose an artificial blood vessel upon acute aortic dissection or surgery of thoracic and abdominal aortic aneurysm, or used for surgery such as gastrointestinal resection and anastomosis, lung resection, bronchorrhaphy, skin closure, etc.

In particular, the medical anastomosis apparatus according to the present invention is used to anastomose blood vessels. Here, the anastomosis of the blood vessels is carried out by overlapping a blood vessel and an artificial blood vessel to be anastomosed, or overlapping an organ and a blood vessel or an organ and another organ, passing a staple clip through the overlapping region and bending the staple clip.

Hereinafter, the present invention will be described in further detail with reference to the accompanying drawings. However, it should be understood that the following description pertains merely to a preferable example for the purpose of illustration only and is not intended to limit the scope of the invention.

Figure 1:
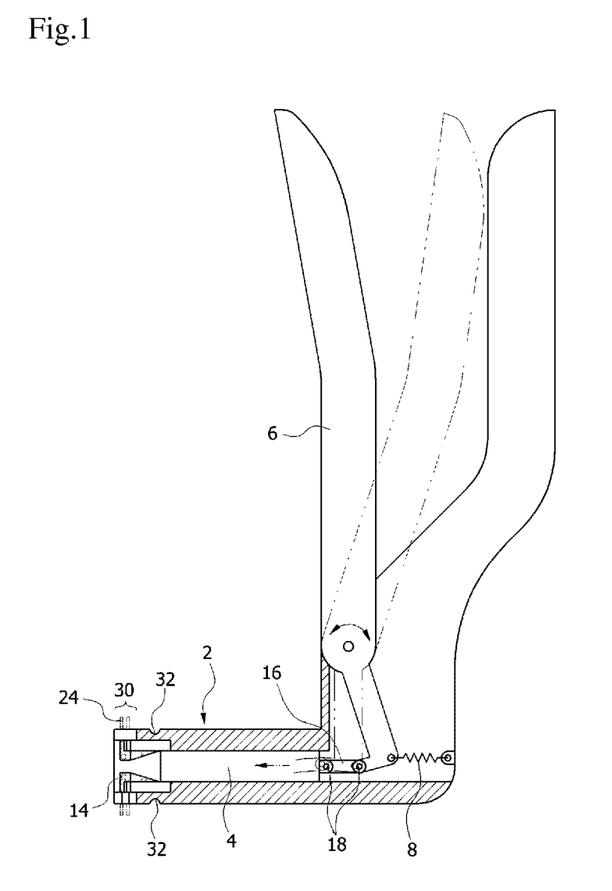
FIG. 1 is a cross-sectional view showing a configuration of a medical anastomosis apparatus according to the present invention.
Figure 2:
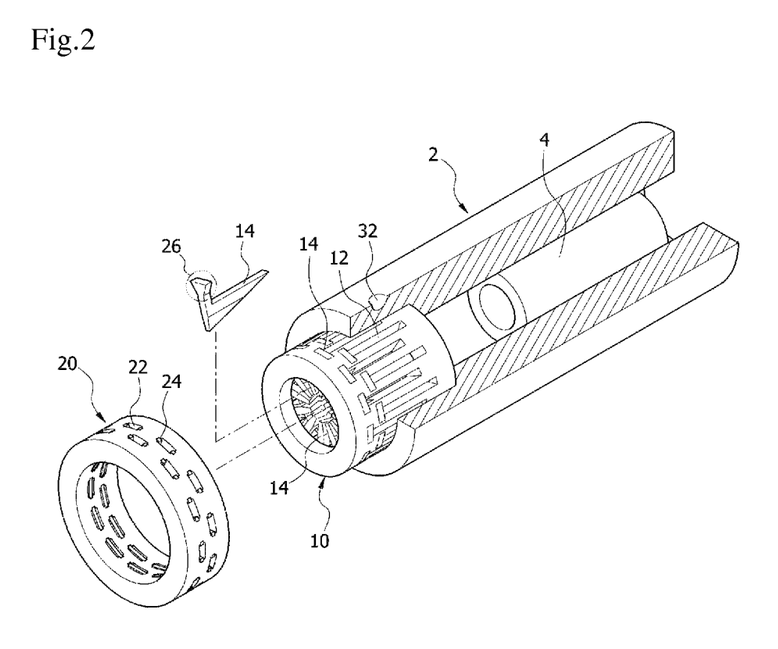
FIG. 2 is a configuration diagram showing the coupling relationship among a pressing rod, a guide member and a staple cartridge which constitute the medical anastomosis apparatus according to the present invention.
Figure 3:
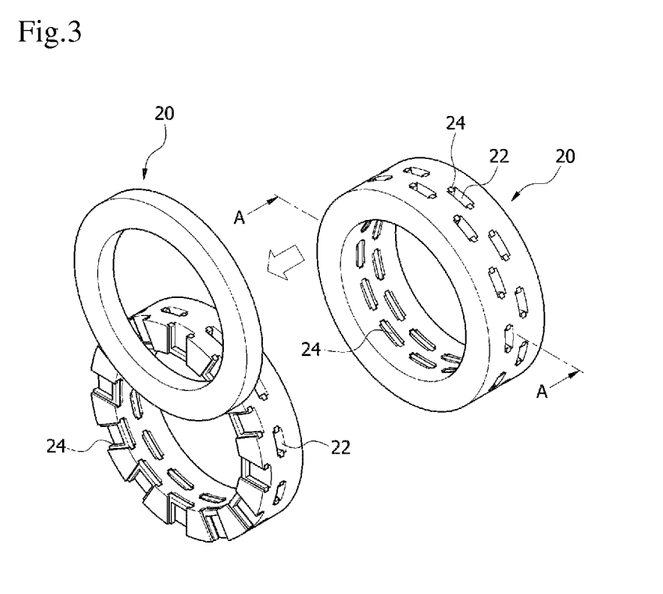
FIG. 3 is a configuration diagram showing the staple cartridge of the medical anastomosis apparatus according to the present invention.
Figure 4:
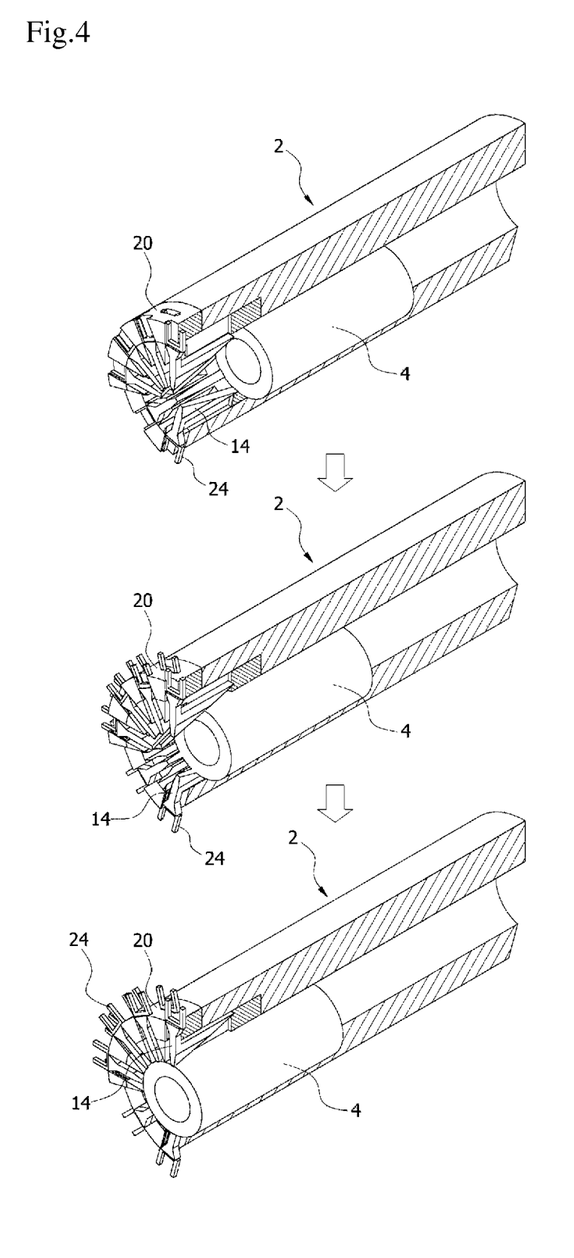
FIG. 4 is a diagram showing an action mechanism of the medical anastomosis apparatus according to the present invention.
Figure 5:
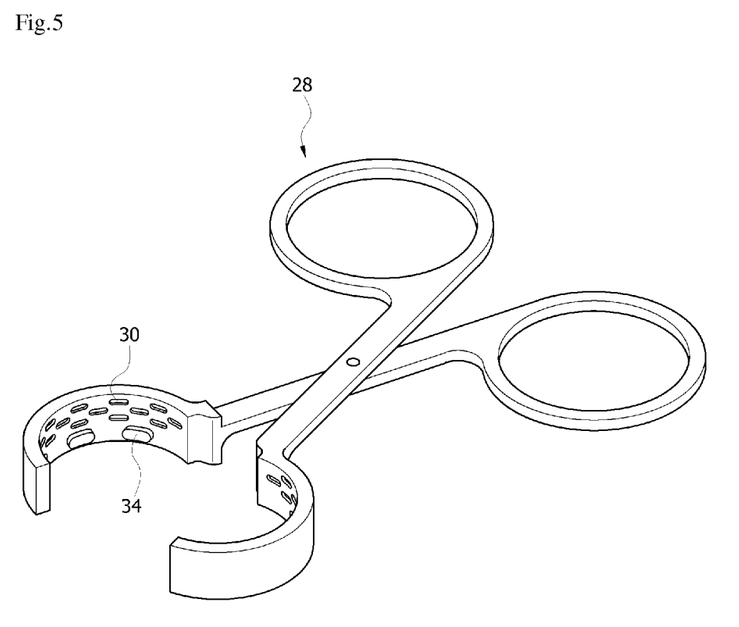
FIG. 5 is a perspective view of a staple clamp according to the present invention.
Figure 6:
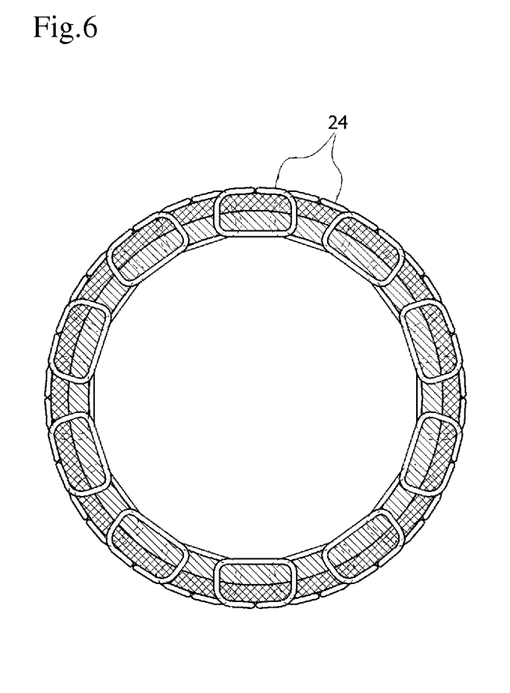
FIG. 6 is a diagram showing a blood vessel anastomosed using the medical anastomosis apparatus according to the present invention.

FIG. 1 is a cross-sectional view showing a configuration of a medical anastomosis apparatus according to the present invention, FIG. 2 is a configuration diagram showing the coupling relationship among a pressing rod, a guide member and a staple cartridge which constitute the medical anastomosis apparatus according to the present invention, FIG. 3 is a configuration diagram showing the staple cartridge of the medical anastomosis apparatus according to the present invention, FIG. 4 is a diagram showing an action mechanism of the medical anastomosis apparatus according to the present invention, FIG. 5 is a perspective view of a staple clamp according to the present invention, and FIG. 6 is a diagram showing a blood vessel anastomosed using the medical anastomosis apparatus according to the present invention.

As shown in FIGS. 1 to 6, the medical anastomosis apparatus according to the present invention includes a cylindrical body 2 which has a hollow portion and extends in a longitudinal direction, a pressing rod 4 which is provided inside the hollow portion of the body 2 to translate along the hollow portion, a knob 6 which is coupled to the pressing rod 4 to provide a driving force to translate the pressing rod 4, a guide member 10 which is inserted into one end of body 2 and simultaneously has a portion exposed from the body and has a pressing unit 14 formed therein to move radially upon translation of the pressing rod 4, and a staple cartridge 20 which is inserted around an outer circumferential surface of the guide member 10 and then coupled to the body 2 and has built-in staple clips 24 that protrude outward upon movement of the pressing unit 14.

The body 2 according to the present invention is configured to have a hollow portion and extends in a longitudinal direction.

In this case, the body 2 may have internally curved coupling grooves 32 formed therein so that a staple clamp 28, particularly, coupling protrusions 34 of the staple clamp 28, can be coupled to a portion of an outer circumferential surface of the body 2.

A plurality of coupling grooves 32 may be provided according to the user's choice.

The pressing rod 4 according to the present invention is provided in the inside of the hollow portion of the body 2 to translate along the hollow portion. Here, typical pressing rods known in the art may be used without particular limitation as long as they are used for this purpose.

The pressing rod 4 may be in a cylindrical form.

The guide member 10 according to the present invention enables the pressing unit 14 provided inside the guide member 10 to move upon translation of the pressing rod 4, and the staple clips 24 of the staple cartridge 20 to protrude outward. Here, the guide member 10 is configured to be inserted into one end of the body 2 and simultaneously has a portion exposed from the body.

Here, the staple cartridge 20 is inserted into a portion of the guide member 10 which is not inserted into the body 2 but exposed outward.

The pressing unit 14 may be formed in a wedge shape, and a plurality of pressing units 14 may be radially formed around the internal center of the guide member 10.

For the wedge-shaped pressing unit 14, when an insert 26 extending in a vertical direction is formed in an upper portion of the pressing unit 14 so that the pressing unit 14 can move perpendicularly to an outer circumferential surface of the body 2, the insert 26 enables the staple clip 24 to protrude outward by pressing the staple clip 24 formed inside the staple cartridge 20.

In this case, when the pressing rod 4 moves through the hollow portion of the body 2, the pressing rod 4 moves along an inclined plane of the wedge-shaped pressing unit 14, and the pressing unit 14 moves in a vertical direction.

Also, the pressing unit 14 may be provided in a plurality of rows along the outer circumferential surface of the guide member 14.

According to one exemplary embodiment, the guide member 10 according to the present invention may include a cylindrical guide member body having a hollow portion configured to give the appearance of the guide member 10, a plurality of guide grooves 12 formed through the body around an outer circumferential surface of the body, and a pressing unit 14 inserted and mounted in the plurality of guide grooves 12.

Here, the guide grooves 12 may be configured to enable the pressing unit 14 to vertically move along the guide grooves 12 upon translation of the pressing rod 4.

Also, a plurality of pressing units 14 provided in the guide member 10 may be radially formed around the internal center of the guide member 10.

Also, the plurality of pressing units 14 may be formed in a plurality of rows around the outer circumferential surface of the guide member 10.

In this case, when the pressing units 14 are formed in a plurality of rows, the plurality of guide grooves 12 configured to guide the respective pressing units 14 are formed at positions corresponding to the pressing units 14.

Meanwhile, the pressing rod 4 according to the present invention is translated so that the pressing rod 4 can be inserted into a hollow portion of the guide member 10. Therefore, the pressing rod 4 may be formed so that the pressing rod 4 can have a smaller outer diameter than an inner diameter of the guide member 10.

The knob 6 according to the present invention is coupled to the pressing rod 4 to provide a driving force to translate the pressing rod 4. Here, typical knobs known in the art may be used without particular limitation as long as they are used for this purpose.

The knob 6 may be configured so that an elastic member 8, for example, a spring, can be coupled to one end of the knob 6. As a result, when a user, for example, an operating physician, pulls the knob 6, the knob 6 enables the pressing rod 4 coupled to one side of the knob 6 to move toward one end of the body 2, preferably, in the direction in which the staple cartridge 20 is coupled to the body 2. When the knob 6 is released after the movement is completed, the knob 6 may return to its original position.

In this case, one side of the elastic member 8 that faces the other side of the elastic member 8 coupled to the knob 6 may be coupled to another knob extending to the body 2.

Also, the knob 6 may act on the lever principle.

According to one specific exemplary embodiment, the knob 6 according to the present invention may be coupled to the pressing rod 4 by means of a link 16.

In this case, the link 16 may be fixed to the knob 6 and the pressing rod 4, which are coupled to both ends of the link 16 in a longitudinal direction, using joints 18.

The staple cartridge 20 according to the present invention is coupled to one end of the body 2, has built-in staple clips 24 that protrude outward upon movement of the pressing unit 14 to allow the staple clips 24 to protrude outward, and functions to anastomose an overlapping region between blood vessels, preferably, a blood vessel and another blood vessel or a blood vessel and an artificial blood vessel, or an overlapping region between an organ and another organ or an organ and a blood vessel.

In this case, the staple cartridge 20 may be inserted around the outer circumferential surface of the guide member 10 coupled to the body 2.

Also, the staple cartridge 20 may be attached to or detached from the body 2.

According to one specific exemplary embodiment, the staple cartridge 20 according to the present invention may include a cylindrical staple cartridge body having a hollow portion configured to give the appearance of the staple cartridge, a plurality of staple grooves 22 formed through the body around an outer circumferential surface of the body, and staple clips 24 inserted into the staple grooves 22.

Here, the staple grooves 22 provide places in which the staple clips 24 are mounted.

Also, the staple grooves 22 guide movements of the staple clip 24 toward blood vessels when the pressing unit 14 moves in a vertical direction upon translation of the pressing rod 4.

Here, the staple clips 24 may be formed in a "⊏" shape, and, when the staple clips 24 are mounted inside the staple grooves 22, the "⊏"-shaped opening may be positioned toward the blood vessels, that is, toward the outer circumferential surface of the staple cartridge 20.

Meanwhile, the plurality of pressing units 14 provided in the guide member 10 according to the present invention may be radially formed around the internal center of the guide member 10. As a result, the staple grooves 22 of the staple cartridge 20 are placed at positions corresponding to the plurality of radially formed pressing units 14.

Also, the plurality of staple grooves 22 may be formed in a plurality of rows around the staple cartridge 20, preferably in an outer circumferential surface of the staple cartridge body.

The medical anastomosis apparatus having the above-described configuration according to the present invention may be used with a clamp, preferably a staple clamp 28, so that an artificial blood vessel to be anastomosed can overlap a blood vessel and the staple clip 24 can pass through an overlapping region of the artificial blood vessel and/or blood vessel and be bent to anastomose the blood vessels.

The staple clamp 28 has clip grooves 30 formed therein, and configured to pick up the body 2 of the medical anastomosis apparatus are smoothly curved inward.

Here, since the clip grooves 30 are formed at positions corresponding to protrusions of the staple clips 24, the staple clips 24 are bent along the clip grooves 30 when the staple clips 24 protrude outward.

In particular, the staple clamp 28 according to the present invention has coupling protrusions 34 formed therein. In this case, the coupling protrusions 34 protrude outward from inside so that the body 2 can be easily coupled to the staple clamp 28, since the coupling protrusions 34 are inserted into the coupling grooves 32 formed at the outer circumferential surface of the body 2 to be curved inward.

In this case, the coupling protrusions 34 are formed in a shape corresponding to the coupling grooves 32 formed at the body 2.

An action mechanism of the medical anastomosis apparatus having such a configuration according to the present invention will be described, as follows. One case in which a blood vessel is anastomosed with another blood vessel or with an artificial blood vessel will be described so as to easily explain the present invention.

First, an operating physician assembles an anastomosis apparatus by combining the staple cartridge 20 to the body 2, inserts the body 2 of the anastomosis apparatus into an overlapping region between a blood vessel and another blood vessel or between a blood vessel and an artificial blood vessel, and positions the body 2 at the overlapping region of the blood vessels to be stapled by the staple cartridge 20.

Next, the staple clamp 28 is positioned over the overlapping region of the blood vessels, that is, the blood vessels in which the staple cartridge 20 is positioned to clamp the blood vessels.

In this case, the staple clamp 28 may be mounted more easily by inserting the coupling protrusions 34 formed in the staple clamp 28 into the coupling grooves 32 formed at the body 2 of the anastomosis apparatus.

Subsequently, the pressing rod 4 coupled to the knob 6 is allowed to move toward the staple cartridge 20 by pulling the knob 6.

In this case, when the pressing rod 4 moves toward the staple cartridge 20, the pressing rod 4 moves toward the hollow portion of the guide member 10 inserted into the hollow portion of the staple cartridge 20.

Then, when the pressing rod 4 moves to be inserted into the hollow portion of the guide member 10, the pressing unit 14 provided in the guide member 10 moves in a vertical direction, and presses the staple clips 24 mounted inside the staple cartridge 20 so that the staple clips 24 can pass through an overlapping region of blood vessels and protrude radially.

Thereafter, the radially protruding staple clips 24 are introduced into clip grooves 30 of the staple clamp 28 that clamps the overlapping region of blood vessels, and bent along the shapes of the clip grooves 30 to staple the blood vessels.

A section of the blood vessels anastomosed by the above-described stapling is shown in FIG. 6.

As shown in FIG. 6, when the medical anastomosis apparatus according to the present invention is used to anastomose a blood vessel with another blood vessel or a blood vessel with an artificial blood vessel, inside and outside of the blood vessels may be securely stitched so that rapid and safe anastomosis can be achieved.

Also, when the staple clips 24 are formed in a plurality of rows, blood vessels may be anastomosed more securely, compared to stapling in a single row.

According to the present invention, the medical anastomosis apparatus can be used to rapidly and safely perform a complicated reinforcing/anastomosis procedure which includes anastomosing a surgical site upon surgery such as gastrointestinal resection and anastomosis, lung resection, bronchorrhaphy or skin closure, or reinforcing an aortic resection site and anastomosing an artificial blood vessel upon acute aortic dissection or surgery of thoracic and abdominal aortic aneurysm, which are classified as lethal diseases.

While the invention has been shown and described with reference to certain exemplary embodiments thereof, it will be understood by those skilled in the art that various changes in form and details may be made therein without departing from the scope of the invention as defined by the appended claims.

What is claimed is:

1. A medical anastomosis apparatus comprising:
    a cylindrical body which has a hollow portion and extends in a longitudinal direction;
    a pressing rod which is provided in the inside of the hollow portion of the body to translate along the hollow portion;
    a knob which is coupled to the pressing rod to provide a driving force to translate the pressing rod;
    a guide member which is inserted into one end of the body and simultaneously has a portion exposed from the body and has pressing units formed therein to move radially upon translation of the pressing rod;
    a plurality of guide grooves which are formed into the body of the guide member along an outer circumferential surface of the body of the guide member;
    said pressing units which are inserted and mounted in the plurality of guide grooves, form radially around the inner portion of the center of the guide member and vertically move toward the outer circumferential surface of the body of the guide member upon translation of the pressing rod; and
    a staple cartridge which is inserted around said outer circumferential surface of the body of the guide member and then coupled to the body and has built-in staple clips that protrude outward upon movement of the pressing units.

2. The medical anastomosis apparatus of claim 1, wherein the pressing units provided in the guide member are wedge shaped.

3. The medical anastomosis apparatus of claim 1, wherein the pressing units are provided in a plurality of rows around the outer circumferential surface of the body of the guide member.

4. The medical anastomosis apparatus of claim 1, wherein the staple cartridge comprises:
    a cylindrical staple cartridge body having a hollow portion;
    a plurality of staple grooves formed through the body around an outer circumferential surface of the staple cartridge body; and
    said built-in staple clips inserted into the staple grooves.

5. The medical anastomosis apparatus of claim 4, wherein the staple grooves are formed in a plurality of rows around an outer circumferential surface of the staple cartridge body.

6. The medical anastomosis apparatus of claim 1, wherein the staple cartridge is attachable to and detachable from the body.

7. The medical anastomosis apparatus of claim 1, further comprising:
    a staple clamp configured to bend the staple clips extruding in a radial direction.

8. The medical anastomosis apparatus of claim 7, wherein the staple clamp has internally curved clip grooves formed inside thereof, the clip grooves being formed at positions corresponding to regions from which the staple clips protrude.

9. The medical anastomosis apparatus of claim 7, wherein coupling grooves formed to be internally curved are formed at one side of the outer circumferential surface of the body, and coupling protrusions are formed inside of the staple clamp at positions corresponding to the coupling grooves so as to be inserted and coupled to the coupling grooves.

\* \* \* \* \*